US00PP18397P2

(12) United States Plant Patent
Zary

(10) Patent No.: US PP18,397 P2
(45) Date of Patent: Jan. 1, 2008

(54) MINIATURE ROSE PLANT NAMED 'JACSEBOY'

(50) Latin Name: *Rosa hybrida*
Varietal Denomination: JACseboy

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 90 days.

(21) Appl. No.: 11/187,344

(22) Filed: Jul. 21, 2005

(51) Int. Cl.
*A01H 5/00* (2006.01)

(52) U.S. Cl. ..... Plt./122

(58) Field of Classification Search ..... Plt./116, Plt./121, 122
See application file for complete search history.

(56) References Cited

PUBLICATIONS

Jackson & Perkins Wholesale, Inc. http://www.jproses.com/code_varieties/product_id=359,351,371,354,367,368,360,358,369,357,379,352,355,361,356,370,362 (2 pages).*

* cited by examiner

*Primary Examiner*—Howard J. Locker
(74) *Attorney, Agent, or Firm*—Klarquist Sparkman LLP

(57) ABSTRACT

Miniature rose plant having very compact but spreading plant habit, blooming constantly in clusters, easily propagated by softwood cuttings and small, disease resistant foliage.

1 Drawing Sheet

Genus and species: *Rosa hybrida.*
Variety denomination: 'JACseboy'.

ORIGIN OF THE INVENTION

The present invention relates to a new and distinct variety of a miniature rose plant named 'JACseboy' which was originated by me by crossing an unnamed white shrub rose (not patented) ('POULcat' (not patented)×'POULcov' (PP10648), with 'DICrevival' (PP8614).

BACKGROUND OF THE INVENTION

The primary objective of this breeding was to produce a new miniature rose variety having the large flower clusters, excellent disease resistance and compact habit of the female parent combined with the bright pink flower color and higher petal count of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very compact but spreading plant habit.
2. Blooms constantly in clusters.
3. Ease of propagation by softwood cuttings.
4. Small, disease resistant foliage.

Asexual reproduction of this new variety by cuttings, as performed at Wasco and Somis, Calif., shows that the foregoing and all other characteristics and distinctions come true to form and are established and transmitted through succeeding propagations.

COMPARISON WITH PARENTS

'JACseboy' has light red to red versus white flowers, ten to fifteen versus five petals and a more spreading habit compared to the female parent. Compared to the male parent, 'JACseboy' is much more compact in habit, has smaller and much more numerous flowers.

COMPARISON WITH SIMILAR VARIETY

The closest variety is 'The Fairy'. 'JACseboy' differs in being more compact in habit, having smaller flowers with fewer petals but similar foliage, disease resistance and flower color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Unnamed White Shrub (unpatented), 'POULcat' (unpatented)×'POULcov' (PP10,648).

*Pollen parent.*—'DICrevival' (U.S. Plant Pat. No. 8,614),

Observations made from January 2003 to September 2004 from plants commencing at three years of age grown in a garden environment at Somis, Calif.

FLOWER

Blooming habit: Continuous.

Bud:

*Size.*—About 10 mm long and 8 mm in diameter when the petals start to unfurl.

*Form.*—The bud form is long, pointed ovoid.

*Color.*—When sepals first divide, bud color is Red Group 46C. When half blown, the upper sides of the petals are Red Group 46A and the lower sides of the petals are Red Group 46C.

*Sepals.*—Color: Upper surface: Green Group 138B. Lower surface: Green Group 138B but often with Greyed-Purple Group 183B. Length: 10 mm. Width: 4 mm. Shape: Subulate. Surface texture: Hoary. There are three normally appendaged sepals. There are two unappendaged sepals with hairy edges.

*Receptacle.*—Color: Green Group 138B, with areas of Greyed-Purple Group 183B where exposed to direct sunlight. Shape: Funnel. Size: Small, about 3 mm long×3 mm wide. Surface: Smooth.

*Peduncle.*—Length: Short, averaging about 25 mm. Surface: Glandular. Color: Green Group 138C, with areas of Greyed-Purple Group 183B where exposed to direct sunlight. Strength: Stiff, erect.

Bloom:

*Size.*—Small. Average open diameter is about 30 mm.

*Borne.*—Several together in pyramidal clusters of 3–15 blooms.

*Stems.*—Strength: Strong. Average length is about 15 cm with a diameter of 3–4 mm.

*Form.*—When first open: Flat. Permanence: Retains its form until the end.

*Petalage.*—Number of petals under normal conditions: 10–15.

*Color.*—The upper sides of the petals are Red Group 46A. The reverse sides of the petals are Red Group 46C. The base of the petals has a small 2mm×2 mm color spot of White Group 155A on the reverse surface and of Yellow Group 4C on the upper surface. The major color on the upper sides is Red Group 46A.

*Variegations.*—There is often a streak of White Group 155A on both petal surfaces.

*Discoloration.*—The general tonality at the end of the first day: No change. At the end of the third day: No change. Further aging: No change.

*Fragrance.*—None.

Petals:

*Texture.*—Thin.

*Shape.*—Obelliptic.

*Surface.*—Smooth.

*Margin.*—Entire. Apex Shape: Rounded. Base Shape: Cuneate.

*Form.*—Flat with tips slightly recurved.

*Arrangement.*—Imbricated.

*Petaloids.*—Number: 0–3. Color: Red Group 46A upper surfaces and lower surfaces Red Group 46 C.

*Persistence.*—Petals drop off cleanly before drying.

*Lastingness.*—On the plant: Short (about 3–4 days). As a cut flower: Short (about 3–4 days).

Reproductive parts:

*Stamens.*—Number: 45–50. Length: 4–5 mm. Anthers: Length: 1 mm. Color: Yellow-Orange Group 15D. Arrangement: Regular around styles. Filaments: Color: Yellow-Orange Group 15C. Length: 3–4 mm. Pollen: Color: Yellow-Orange Group 22C.

*Pistils.*—Number: 10–15. Length: 2–3 mm. Styles: Color: Greyed-Purple Group 184D. Length: 1–2 mm. Stigmas: Color: Greyed-Yellow Group 161D. Length: 1 mm.

*Hips.*—None observed.

PLANT

Form: Bush.

Growth: Vigorous, dwarf, branching, compact.

Age at Maturity: One year.

Mature Plant: Height: 45 cm. Width: 45 cm.

Rootstock: Own roots.

Foliage: Number of leaflets on normal mid-stem leaves: 5 to 7.

*Size.*—Small. About 8–9 cm long×4–5 cm wide.

*Quantity.*—Normal.

*Color.*—New foliage: Upper side: Greyed-Purple Group 183A. Lower side: Greyed-Purple Group 183D. Old foliage: Upper side: Green Group 136B. Lower side: Green Group 138A.

Leaflets:

*Size.*—About 20–25 mm long×10–15 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Yellow-Green Group 146B.

*Petiole rachis.*—Color: Yellow-Green Group 146B. Underside: Rough with prickles.

*Auricles.*—None.

*Stipules.*—Length: 8 mm; serrated.

*Disease resistance.*—Resistant to rust and powdery and downy mildew but susceptible to blackspot under normal growing conditions.

*Pest resistance.*—Not observed.

*Vein color.*—Green Group 138A.

*Venation pattern.*—Reticulate.

Wood:

*New wood.*—Color: Greyed-Purple Group 183A. Bark: Smooth.

*Old wood.*—Color: Yellow-Green Group 146B. Bark: Smooth.

Prickles:

*Quantity.*—On main canes from base: 4 or 5 per 10 cm. On laterals from main canes: 4 or 5 per 10 cm.

*Form.*—Straight to slightly hooked downward.

*Length.*—5–6 mm.

*Color when Young.*—Greyed-Purple Group 183C.

*Color when Mature.*—Grey-Brown Group 199C.

Small prickles:

*Quantity.*—On main stalks: None. On laterals: None.

Winter Hardiness: Hardy to Zone 5.

I claim:

1. A new and distinct variety of a rose plant of the miniature class, substantially as herein shown and described, characterized particularly by its very compact but spreading plant habit, blooming constantly in clusters, ease of propagation by softwood cuttings and small, disease resistant foliage.

* * * * *

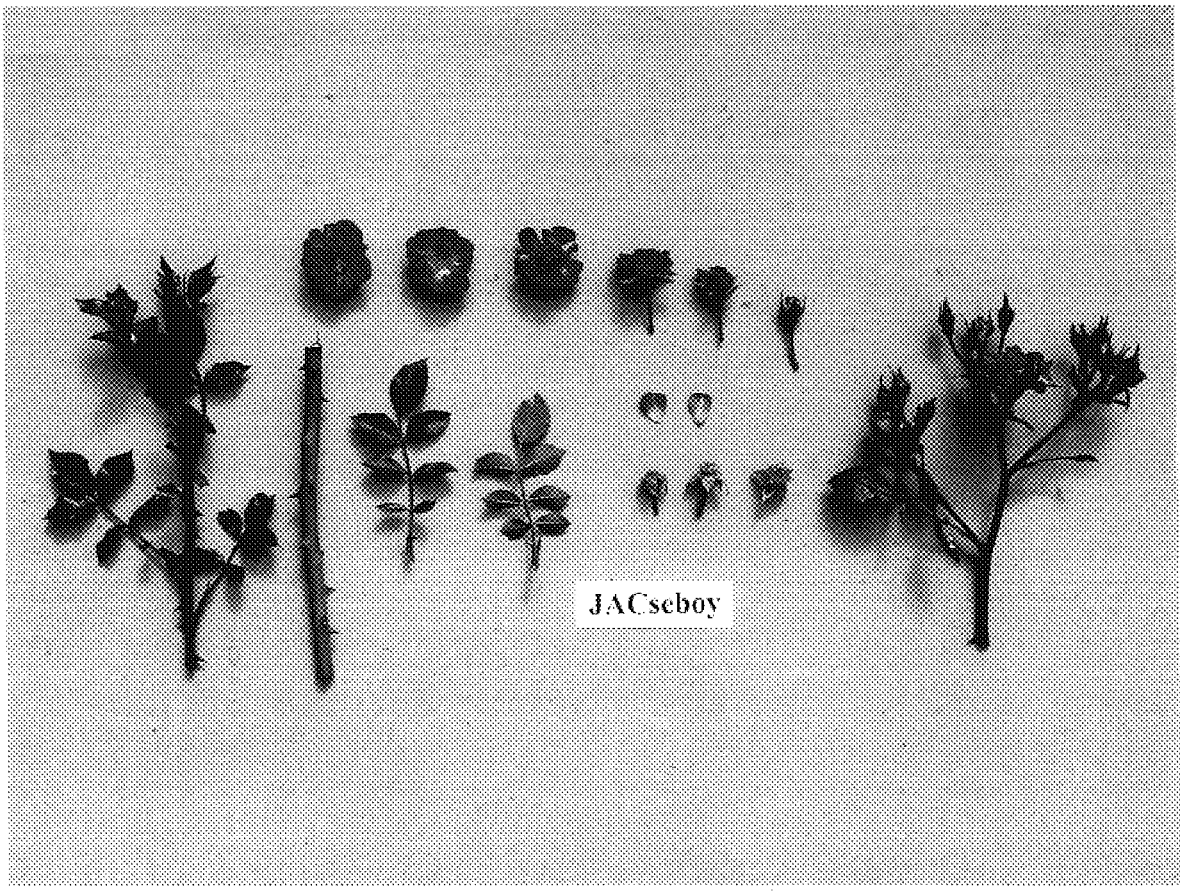
JACseboy